US008003109B2

(12) United States Patent
Bottazzi et al.

(10) Patent No.: US 8,003,109 B2
(45) Date of Patent: Aug. 23, 2011

(54) PHARMACEUTICAL COMPOSITIONS CONTAINING THE LONG PENTRAXIN PTX3

(75) Inventors: Barbara Bottazzi, Milan (IT); Martino Introna, Milan (IT); Alberto Mantovani, Milan (IT); Annunciata Vecchi, Milan (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

(21) Appl. No.: 11/882,180

(22) Filed: Jul. 31, 2007

(65) Prior Publication Data

US 2008/0015153 A1  Jan. 17, 2008

Related U.S. Application Data

(62) Division of application No. 09/555,473, filed on May 31, 2000, now abandoned.

(30) Foreign Application Priority Data

Dec. 19, 1997  (IT) ................................. RM97A0796

(51) Int. Cl.
 *A61K 39/00* (2006.01)
(52) U.S. Cl. .................................................. 424/185.1
(58) Field of Classification Search .................. None
 See application file for complete search history.

(56) References Cited

U.S. PATENT DOCUMENTS

| | | | |
|---|---|---|---|
| 4,751,242 A | | 6/1988 | Calvani et al. |
| 5,426,181 A | * | 6/1995 | Lee et al. .................... 536/23.5 |
| 5,632,983 A | | 5/1997 | Hadden et al. |
| 5,939,423 A | | 8/1999 | Karlin et al. |
| 6,344,320 B1 | | 2/2002 | Rothschild et al. |
| 6,872,541 B2 | | 3/2005 | Mills |
| 7,041,648 B2 | | 5/2006 | Mantovani |
| 7,683,032 B2 | | 3/2010 | Carminati et al. |
| 2004/0023879 A1 | | 2/2004 | Mantovani et al. |
| 2004/0029803 A1 | | 2/2004 | Mantovani et al. |
| 2004/0137544 A1 | | 7/2004 | Latini et al. |
| 2004/0198655 A1 | | 10/2004 | Mantovani |
| 2005/0152876 A1 | | 7/2005 | Mantovani |
| 2006/0148001 A1 | | 7/2006 | Mantovani |
| 2006/0286617 A1 | | 12/2006 | Latini et al. |
| 2007/0098722 A1 | | 5/2007 | Bottazzi et al. |
| 2009/0275508 A1 | | 11/2009 | Romani et al. |
| 2009/0286726 A1 | | 11/2009 | Carminati et al. |
| 2010/0209442 A1 | | 8/2010 | Carminati et al. |

FOREIGN PATENT DOCUMENTS

| | | | |
|---|---|---|---|
| WO | WO 92/12176 | * | 7/1992 |
| WO | 93/21313 | | 10/1993 |
| WO | 99/32516 | | 1/1999 |
| WO | 2004/094991 | | 11/2004 |
| WO | 2006/037744 | | 4/2006 |

OTHER PUBLICATIONS

Metzler et al. 'Solution structure of human CTLA-4 and delineation of a CD80/CD86 binding site conserved in CD28.' Nature Structural Biol. 4:527-531, 1997.*
Gewurz et al. 'Structure and function of the pentraxins.' Curr. Opin. Immunol. 7:54-64, 1995.*
Reading et al.'Antiviral activity of the long chain pentraxin PTX3 against influenza viruses.' J. Immunol. 180:3391-3398, 2008.*
Mairuhu et al. 'Elevated plasma levels of the long pentraxin, pentraxin 3, in severe dengue virus infections.' J. Med. Virol. 76:547-552, 2005.*
Soares et al. 'Dual function of the long pentraxin PTX3 in resistance against pulmonary infection with *Klebsiella pneumoniae* in transgenic mice.' Microbes and Infection. 8:1321-1329, 2006.*
He et al.'Long pentraxin 3 in pulmonary infection and acute lung injury.' Am. J. Phsiol. Lung. Cell. Mol. Physiol. 292:L1039-L1049, 2007.*
Nauta, A. "Biochemical and Function Characterization of the Interaction . . . " Eur. J. Immunol., vol. 33, pp. 465-473, 2003.
Hamazaki, H. "Structure and Significance of n-Linked Sugar Unit . . . ", Biochemicica et Biophysica Acts., vol. 1037, pp. 435-438, 1990.
Siripont, J. et al. "Receptor-Mediated Binding of the Acute-Phase . . . ", Cellular Immunology, vol. 117, pp. 239-252, 1988.
Tennent, G. et al. "Glycobiology of the Pentraxins", Biochemical Society Transactions, vol. 22, No. 1, pp. 74-79, 1994.
Camozzi et al., Arterioscler Thromb Vasc Biol. Sep. 2005;25(9):1837-42. Epub Jul. 14, 2005.
Souza et al., Am J Pathol. Apr. 2009;174(4):1309-18. Epub Mar. 12, 2009.
Bassi et al., Clin Rev Allergy Immunol. Nov. 18, 2008. [Epub ahead of print], 8 pages.
Bevelacqua et al., Int J Mol Med. Sep. 2006;18(3):415-23.
Kataoka et al., Atherosclerosis. Mar. 2008;197(1 ):368-74. Epub Jul. 19, 2007.
Luchetti et al., Clin Exp Immuno12000, 119:196-202.
Rolph et al., Arterioscler Thomb Vasc Bioi 2002, 22: 1-5.
Polentarutti et al., "Interferon-Gamma Inhibits Expression of the Long Pentraxin PTX3 in Rheumatoid Arthritis (RA)" European J, Immunol., vol. 28, 1998, pp. 496-501.
Alles et al. "Inducible expression of PTX3, a new member of the pentraxin family, in human mononuclear phagocytes" Blood 84:3483-3493 (1994).
Berry et al. "Mesenchymal stem cell injection after mycardial infarction improves myocardial compliance" Am. J. Physiol. Heart Circ. Physiol. 290:H2196-H2203 (2006).
Bottazzi et al. "Preliminary biochemical and biological characterization of PTX3, a new member of the pentraxin gene family" Cytokine 9:903 (1997).
Bottazzi et al. "Multimer formation and ligand recognition by the long pentraxin PTX3. Similarities and differences with the short pentraxins C-reactive protein and serum amyloid P component" J. Biol. Chem. 272:32817-32823 (1997).
Breviario et al. "Interleukin-1-inducible genes in endothelial cells. Cloning of a new gene related to C-reactive protein and serum amyloid P component" J. Biol. Chem. 267:22190-22197 (1992).
"Carboxymethylcellulose Sodium" in The Merck Index, Eleventh Edition, p. 278 (1989).

(Continued)

*Primary Examiner* — Nora Rooney
(74) *Attorney, Agent, or Firm* — Lucas & Mercanti, LLP

(57) ABSTRACT

Pharmaceutical compositions are described containing a long pentraxin PTX3, particularly human PTX3, for the therapy of infectious and inflammatory or tumor diseases; expression vectors containing cDNA coding for PTX3; recombinant host cells transfected with such vectors; a method for producing substantial amounts of PTX3 involving the culturing of such cells, and the use of said vectors in the gene therapy of tumors.

1 Claim, 2 Drawing Sheets

OTHER PUBLICATIONS

"Chapter 3—Vitamin Deficiency, Dependency, and Toxicity" and "Chapter 202—Coronary Artery Disease" in The Merck Manual, pp. 48-49 and 1660-1661, 17th Edition, 1999.

"Choline Chloride" International Chemical Safety Card 0853, two pages (1995).

Dai et al. "A therapeutic model for advanced endometrial cancer: Systemic progestin in combination with local adenoviral-mediated progesterone receptor expression" Mol. Cancer Ther. 4:169-175 (2005).

Dictionary definition of "excipient" from internet: dict.die.net (2003).

Dictionary definition of "excipient" from Butterworths Medical Dictionary, Second Edition, p. 628 (1978).

"Dulbecco's MEM Modified Formulation" ATCC Catalog No. 30-2002 (2002).

"Folic Acid" from internet: suprahealth.com, three pages (2003).

Fordham et al. "Definition of Frequently Used Terms in Regulatory Affairs and Quality Assurance" Albany Molecular Research, Technical Reports, 3:1/11-11/11 (1999).

Gewurz et al. "Structure and function of pentraxins" Curr. Opin. Immunol. 7:54-64 (1995).

"Inositol (Vitamin B8)" in Herb Index from internet: blueprint.bluecrossmn.com, 5 pages (2003).

Introna et al. "Cloning of mouse PTX3 a new member of the pentraxin gene family expressed at extrahepatic sites." Blood 87:1862-1872 (1996).

Mikayama et al. "Molecular cloning and functional expression of a cDNA encoding glycosylation-inhibiting factor" Proc. Natl. Acad. Sci. USA 90:10056-10060 (1993).

Moore et al. "Temporal dissociation between lithium-induced changes in frontal lobe myo-inositol and clinical response in manic-depressive illness" (abstract, two pages) Am. J. Psychiatry 156:1902-1908 (1999).

Ngo et al. in The Protein Folding Problem and Tertiary Structure Prediction, Merz et al. (eds.), Birkhauser, Boston, MA, pp. 433 and 492-495 (1994).

Skolnick et al. "From genes to protein structure and function: Novel applications of computational approaches in the genomic era" Trends in Biotechnol. 18: 34-39 (2000).

"Stability testing of new drug substances and products Q1A (R2)" in ICH Harmonised Tripartite Guideline from Int'l Conference on Harmonisation of Technical Requirements for Registration of Pharmaceuticals for Human Use, p. 18 (2003).

Therapeutic Category and Biological Activity Index from internet: www.merckbooks.com, The Merck Index, pp. THER-1 and THER-26 (2002).

Vouret-Craviari et al. "Expression of a long pentraxin, PTX3, by monocytes exposed to the mycobacterial cell wall component lipoarabinomannan" Infect. Immun. 65:1345-1350 (1997).

* cited by examiner

PHARMACEUTICAL COMPOSITIONS CONTAINING THE LONG PENTRAXIN PTX3

This application is a division of application Ser. No. 09/555,473, filed May 31, 2000, now abandoned; which is a continuation of application Ser. No. PCT/IT98/00364, filed Dec 16, 1998.

The present invention relates to pharmaceutical compositions containing the long pentraxin PTX3 (PTX3) or one of its functional derivatives. In particular, the invention relates to the aforesaid compositions for the therapy of infectious and inflammatory diseases or tumours.

The invention also relates to expression vectors containing the complete cDNA sequence coding for PTX3 or one of its functional derivatives, recombinant host cells transfected with such expression vectors and a method for producing PTX3 or one of its functional derivatives. Further, the invention relates to gene therapy methods for the treatment of tumours, based on the use of the aforesaid expression vectors.

To date, we have yet to fully understand the biological function of PTX3, a protein which is expressed in various types of cells, most notably in mononuclear phagocytes and endothelial cells, after exposure to the inflammatory cytokines Interleukin 1beta (IL-1beta) and Tumour Necrosis Factor alpha (TNF-alpha).

To date, there has also been no description of any therapeutic use of PTX3 or of its functional derivatives.

PTX3 consists of two structural domains, an N-terminial unrelated to any known molecule, and a C-terminal similar to the short pentraxins such as C-reactive protein (CRP). A substantial degree of similarity has been found between human PTX3 (hPTX3) and animal PTX3s.

The PTX3 gene is located on chromosome 3 of the mouse in a region similar to the human 3q region (q24-28), in agreement with the documented location of hPTX3 in the 3q 25 region. Furthermore, mouse PTX3 (mPTX3) (Introna M., Vidal Alles V., Castellano M., Picardi G., De Gioia L., Bottazzi B., Peri G., Breviario F., Salmona M., De Gregorio L., Dragani T. A., Srinivasan N., Blundell T. L., Hamilton T. A. and Mantovani A.: Cloning of mouse PTX3, a new member of the pentraxin gene family expressed at extrahepatic sites. Blood 87 (1996) 1862-1872) is very similar to hPTX3 in terms of organisation, location and sequence (Breviario F., d'Aniello E. M., Golay J., Peri G., Bottazzi B., Bairoch A., Saccone S., Marzella R., Predazzi V., Rocchi M., Della Valle G., Dejana E., Mantovani A., Introna M.: Interleukin-1-inducible genes in endothelial cells. Cloning of a new gene related to C-reactive protein and serum amyloid P component. J. Biol. Chem. 267:22190, 1992).

In particular, the degree of identity between the sequences is 82% between the human and mouse gene and reaches 90% if conservative substitutions are considered.

The high degree of similarity between the hPTX3 and mPTX3 sequences is a sign of the high degree of conservation of pentraxin during evolution (Pepys M. B., Baltz M. L.: Acute phase proteins with special reference to C-reactive protein and related proteins (pentraxins) and serum amyloid A protein. Adv. Immunol. 34:141, 1983).

CRP is a marker for immuno-inflammatory and infectious disease. After a trauma, a lesion or infection of a tissue triggers off, in the affected subject, a complex series of reactions aimed at preventing extension of the damage, at destroying the infecting organism and at activating the repair process in order to restore normal function. This process constitutes the so-called acute-phase response, and the main marker currently used for the acute-phase response is CRP. In normal human serum, in fact, it is present in concentrations of less than 10 µg/ml, but can increase more than 1,000-fold in response to a trauma or inflammation (Koj A.: "Acute phase reactants" in "Structure and Function of Plasma Proteins". Allison A., ed. Plenum Press, New York, 1974, pp. 73-131).

Previous therapeutic uses of CRP are already known. For instance, U.S. Pat. No. 4,857,314 dated Aug. 8, 1989 discloses the use of CRP in combination with TNF for the treatment of tumours.

International patent application PCT/US94/02181 dated 24 Feb. 1994 discloses mutants of CRP which are useful for the preparation of diagnostic kits for determining immunocomplexes in biological fluids and for the treatment of viral and microbial diseases, tumours and endotoxic shock.

International patent application PCT/US94/09729 dated 26Aug. 1994 also discloses mutants of CRP which are useful for the preparation of diagnostic kits and for the treatment of viral and microbial diseases and tumours.

The ability of PTX3 to recognise and bind specifically to ligands which are also recognised by short pentraxins has been evaluated in vitro using purified recombinant PTX3. Short pentraxins such as CRP and SAP (serum amyloid P component) are characterised by their ability to recognise and bind in a calcium-dependent manner to a broad spectrum of ligands, including phosphocholine, phosphoethanolamine, many sugars, the best characterised of which is an agarose derivative rich in pyruvate [methyl 4-6-O-(1-carboxyethylidene)-beta-D-galacto-pyranoside] or MOβDG, complement fragments and proteins of the extracellular matrix, particularly fibronectin and type IV collagen. Unlike the short pentraxins, PTX3 is unable to bind either calcium (assessed by Inductive Coupled Plasma/Atomic Emission Spectroscopy) or phosphocholine, phosphoethanolamine or MOβDG. Moreover, PTX3 is unable to bind extracellular matrix proteins such as fibronectin or type IV collagen. On the other hand, PTX3 is capable of binding the C1q complement fragment which is also recognised by the short pentraxins (Table 1). It should be stressed, however, that, whereas CRP and SAP have to be cross-linked to bind C1q, PTX3 is capable of recognising and binding this complement fragment in the naturally occurring form.

Surprisingly, it has now been found that the long pentraxin PTX3 or its functional derivatives are useful therapeutic agents, particularly for the therapy of infectious and inflammatory diseases or tumours.

What is meant by "long pentraxin PTX3" is any long pentraxin PTX3, i.e. regardless of its natural (human or animal) or synthetic origin. Human long pentraxin PTX3 (see sequence 1 and FIG. 5) is the preferred form.

A convenient method of producing substantial amounts of long pentraxin PTX3 or one of its functional derivatives consists in preparing expression vectors (e.g. plasmids) containing the complete cDNA sequence coding for PTX3 or one of its functional derivatives and in using these to transfer eukaryotic cells in culture (e.g. Chinese hamster ovary cells, CHO). After cloning the recombinant host cells thus transfected, the cell clone capable of producing the highest levels of PTX3 is selected.

According to the present invention, the above-mentioned expression vectors containing the cDNA sequence coding for long pentraxin PTX3 are also utilised in gene therapy methods for the treatment of tumour conditions.

A first gene therapy method consists in:
a) taking samples of cells from a patient suffering from a tumour;
b) transfecting these cells with an expression vector containing the complete cDNA sequence coding for long pentraxin PTX3 or one of its functional derivatives; and c) inoculating the tumour patient with these transfected cells.

A second gene therapy method for the treatment of tumours consists in:
a) preparing an expression vector of viral origin (such as an adenovirus or retrovirus) containing the complete cDNA sequence coding for long pentraxin PTX3 or one of its functional derivatives; and
b) injecting the tumour affected patient with the expression vector thus obtained.

Though the mechanism of action of PTX3 or its functional derivatives has yet to be definitively clarified, their anticancer activity in any event is not attributable to a direct cytolytic or cytostatic effect on the tumour cells, but rather to mechanisms mediated by the host and related to the leukocyte recruitment ability exerted by these compounds, as will be described below.

There now follows a description of the experimental procedures and results are reported demonstrating the unexpected activity of the compounds according to the invention described herein.

Production of recombinant PTX3: a fragment containing the complete cDNA sequence of human PTX3 (sequence 2 and FIG. 6) was subcloned in the Bam H1 site of the expression vector pSG5 (FIG. 1) (Stratagene, La Jolla, Calif., USA) and transfected in CHO cells using the precipitated calcium procedure. A clone selected in G418, capable of producing large amounts of PTX3, was used as a source from which the protein was purified by chromatography by means of ion exchange and gel filtration.

Binding of PTX3 to C1q: the binding of PTX3 to C1q was assessed in an ELISA system. A 96-well plate was covered with 250-500 ng of C1q per well (one night at 4° C.) and then washed with PBS with $Ca^{++}$ and $Mg^{++}$ containing 0.05% Tween 20 (PBS). The wells were then blocked with 5% milk in PBS (2 h at room temperature) and subsequently incubated with variable concentrations of PTX3 (30 min at 37° C.). After a further series of washings, the plate was incubated with a rat monoclonal antibody to PTX3 (1 h at room temperature) and then with the second antibody, a peroxidase-conjugated rat anti-IgG antibody (1 h at room temperature). After washing, chromogen was added and absorbance was read at 405 nm using an automatic plate reader. In a number of experiments, the wells were covered with PTX3 and C1q binding was evaluated using an anti-C1q antibody.

Biotinylated protein was used to determine the C1q binding affinity. PTX3 was biotinylated according to standard procedures using an activated biotin modified by the addition of a "spacer arm". (SPA—Società Prodotti Antibiotici).

FIGS. 2(A) and 2(B) give the C1q binding and binding affinity results. These results show the very substantial degree of C1q binding and binding affinity of PTX3.

Leukocyte recruitment: the leukocyte recruitment induced by PTX3 was studied in vivo in the subcutaneous pocket system. The subcutaneous pocket was induced in the experimental animal by means of two subcutaneous injections of 5 mL of air into the animnal's back with an intervening interval of three days. On day 6, 1 µg of PTX3 in 0.5% carboxymethylcellulose was administered into the pocket. After 4 h, the animals were anaesthetised and the pocket was washed with 1 mL of saline solution. The washing liquid was recovered and was submitted to a total count and a differential count of the cells present.

The results obtained are reported in FIG. 3 and show the substantial leukocyte recruitment capacity of PTX3 in normal animals, whereas FIG. 4 shows the results obtained in genetically modified animals, without C1q, in which the leukocyte recruitment is significantly lower.

Anticancer activity: a line of murine mastocytoma P815 was co-transfected by electroporation with the expression vector pSG5 containing the cDNA of human PTX3 or its antisense and the vector pSV2 which endows the transfected cells with neomycin resistance. After selection with neomycin 0.5 mg/mL, the cells were cloned by limit dilution.

To assess the production of PTX3, $2.5 \times 10^5$ cells were cultivated in 200 µL of RPMI+3% FCS for 24 h and the supernatant was tested by ELISA. The clones obtained produced protein levels ranging from 1 to 35 ng/mL, while the clones containing the antisense produced no measurable levels of PTX3. The clones considered showed the same growth rate in vivo.

Male DBA/2N CrlBR mice aged 8-10 weeks were subcutaneously injected with $1 \times 10^5$ cells of P815 PTX3-producing clones or with clones containing the antisense gene. The mice were monitored 3 times daily for occurrence of tumours and once daily for survival.

The results obtained are reported in Table 2 and show the efficacy of PTX3, in this experimental model of gene therapy, in bringing about healing of the animals and complete rejection of the tumour after the take of the inoculated tumour cells.

These results are statistically significant with $p < 0.01$ (Fisher test) both as compared to controls and to the group treated with the antisense.

In the light of these results it is clear that the anticancer activity reported above correlates closely with the leukocyte recruitment which occurs in the mouse as a result of recognition of the C1q by PTX3. In genetically modified mice, no such leukocyte recruitment occurs. The leukocyte recruitment capacity, on the basis of the anticancer activity of the compounds according to the invention, indicates that these compounds may also have a useful application in the treatment of diseases caused by pathogens such as bacteria, fungi, protozoa or viruses.

TABLE 1

PENTRAXIN BINDING ABILITY TO VARIOUS LIGANDS

|  | CRP | SAP | PTX3 |
| --- | --- | --- | --- |
| $Ca^{2+}$ | + | + | − |
| Phosphocholine | + | − | − |
| Phosphoethanolamine | + | + | − |
| MOβDG | − | + | − |
| C1q | + | + | + |
| Type IV collagen | ND | + | − |
| Fibronectin | ND | + | − |

ND: test not performed

TABLE 2

IN VIVO ANTICANCER ACTIVITY OF PTX3

| Clone[1] | Reject[2] |
| --- | --- |
| Parent P815 (control) | 4/25 |
| P815-AS1 (antisense) | 3/8 |
| P815-PTX3-1 (sense) | 14/14* |

[1] $1 \times 10^5$ cells of the clone indicated were injected subcutaneously.
[2] Number of animals that definitely reject the tumour out of total number of animals in which it took.
*$p < 0.01$ as compared both to mice treated with parent cells and to mice treated with cells of the antisense clones (Fisher test).

Figure 1:
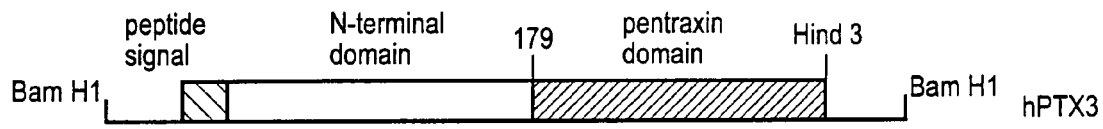
FIG. 1: A fragment containing the complete cDNA sequence of human PTX3 was subcloned in the Bam H1 site of the expression vector pSG5.
Figure 2A:
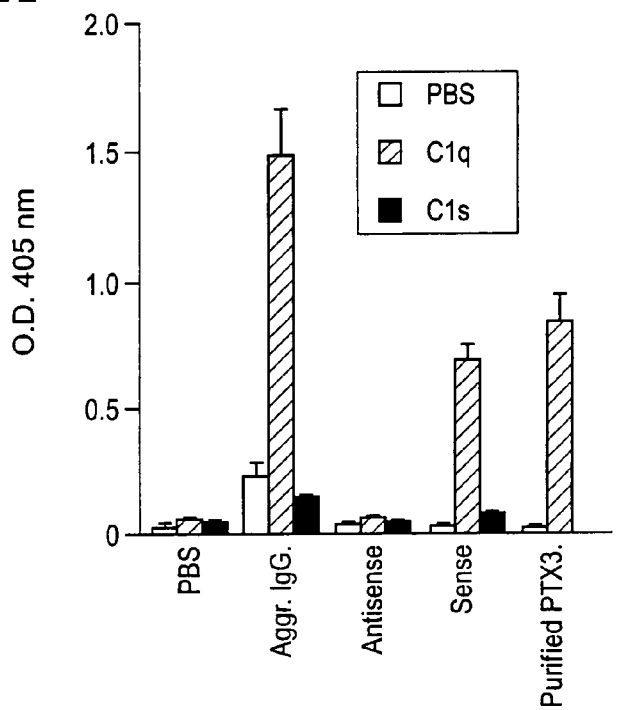
FIG. 2: PTX3 binding to C1q. Panel A shows the binding of the supernatant of the culture containing PTX3 (sense) and of the purified protein to C1q and C1s immobilised on plate. The binding is assessed as optical density (O.D.) at 405 nm. Panel B shows the saturation curve obtained with the biotinylated protein. The kinetic parameters were calculated using the non-linear fitting statistical method.
Figure 2B:
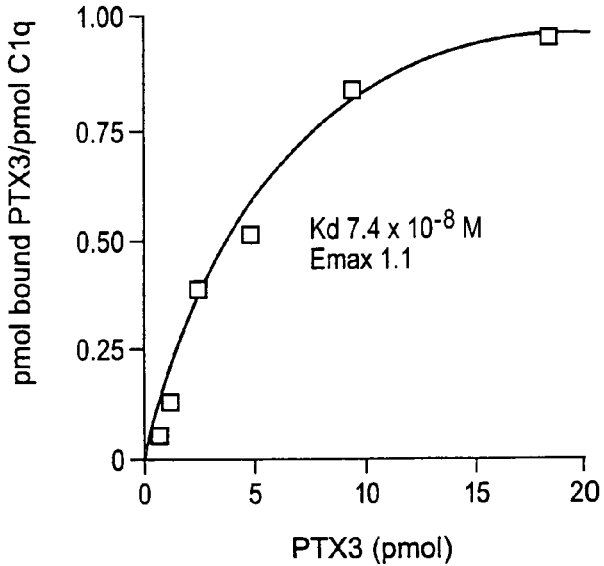
Figure 3:
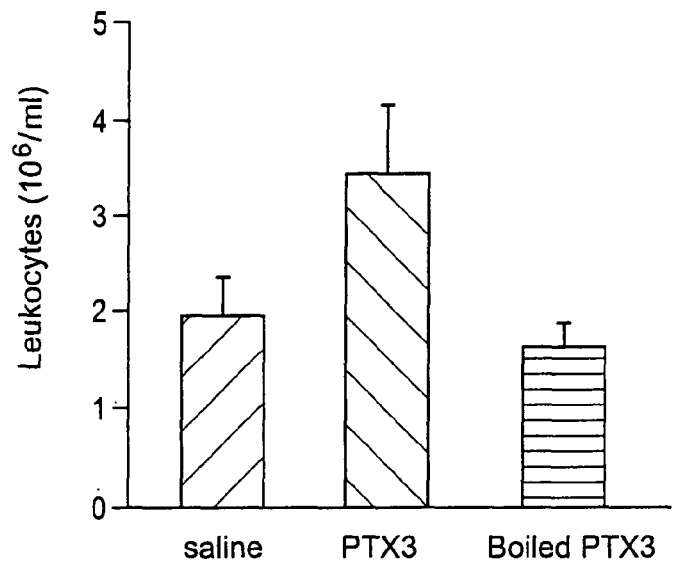
FIG. 3: PTX3-induced leukocyte recruitment: 1 µg of PTX3 is injected into a subcutaneous pocket induced in the back of CD1 mice by inoculation of 5 ml of air.
Figure 4:
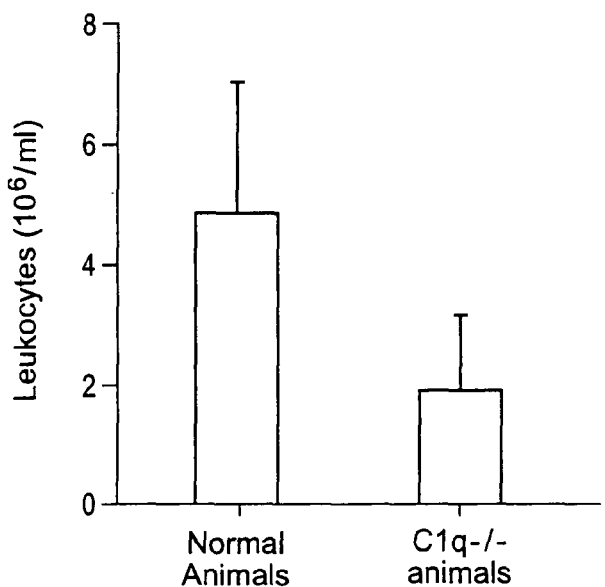
FIG. 4: PTX3-induced leukocyte recruitment in normal animals and in genetically modified animals without C1q. PTX3 is injected into a subcutaneous induced on the back of the animals.

Sequence 1: Amino acid sequence of human PTX3. The underlined amino acids constitute the peptide signal. Mature hPTX3 consists of 364 amino acids.

Sequence 2: Nucleotide sequence of fragment of cDNA of human PTX3. Upper case letters denote nucleotides coding for the protein, while lower case letters denote regions at 3' and 5' not translated but present in the construct.

The invention claimed is:

1. A method for treating an infectious disease, said method comprising administering a long pentraxin PTX3 having the sequence of SEQ ID NO: 1, in a pharmaceutically acceptable excipient to an individual in need of said treatment, wherein said infectious disease is caused by a fungi.

* * * * *

SEQUENCE LISTING

<160> NUMBER OF SEQ ID NOS: 2

<210> SEQ ID NO 1
<211> LENGTH: 381
<212> TYPE: PRT
<213> ORGANISM: Homo sapiens

<400> SEQUENCE: 1

```
Met His Leu Leu Ala Ile Leu Phe Cys Ala Leu Trp Ser Ala Val Leu
 1               5                   10                  15

Ala Glu Asn Ser Asp Asp Tyr Asp Leu Met Tyr Val Asn Leu Asp Asn
             20                  25                  30

Glu Ile Asp Asn Gly Leu His Pro Thr Glu Asp Pro Thr Pro Cys Asp
         35                  40                  45

Cys Gly Gln Glu His Ser Glu Trp Asp Lys Leu Phe Ile Met Leu Glu
     50                  55                  60

Asn Ser Gln Met Arg Glu Arg Met Leu Leu Gln Ala Thr Asp Asp Val
 65                  70                  75                  80

Leu Arg Gly Glu Leu Gln Arg Leu Arg Glu Glu Leu Gly Arg Leu Ala
                 85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
        115                 120                 125

Arg Arg Leu Ala Arg Met Glu Gly Ala Glu Ala Gln Arg Pro Glu Glu
    130                 135                 140

Ala Gly Arg Ala Leu Ala Ala Val Leu Glu Glu Leu Arg Gln Thr Arg
145                 150                 155                 160

Ala Asp Leu His Ala Val Gln Gly Trp Ala Ala Arg Ser Trp Leu Pro
                165                 170                 175

Ala Gly Cys Glu Thr Ala Ile Leu Phe Pro Met Arg Ser Lys Lys Ile
            180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
    210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Gly Glu Glu Asn Lys Leu
                245                 250                 255

Val Ala Glu Ala Met Val Ser Leu Gly Arg Trp Thr His Leu Cys Gly
            260                 265                 270

Thr Trp Asn Ser Glu Glu Gly Leu Thr Ser Leu Trp Val Asn Gly Glu
        275                 280                 285
```

```
Leu Ala Ala Thr Thr Val Glu Met Ala Thr Gly His Ile Val Pro Glu
    290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
            325                 330                 335

Asn Ile Trp Asp Ser Val Leu Ser Asn Glu Glu Ile Arg Glu Thr Gly
        340                 345                 350

Gly Ala Glu Ser Cys His Ile Arg Gly Asn Ile Val Gly Trp Gly Val
    355                 360                 365

Thr Glu Ile Gln Pro His Gly Gly Ala Gln Tyr Val Ser
370                 375                 380

<210> SEQ ID NO 2
<211> LENGTH: 1404
<212> TYPE: DNA
<213> ORGANISM: Homo sapiens

<400> SEQUENCE: 2
ctcaaactca gctcacttga gagtctcctc ccgccagctg tggaaagaac tttgcgtctc      60
tccagcaatg catctccttg cgattctgtt ttgtgctctc tggtctgcag tgttggccga     120
gaactcggat gattatgatc tcatgtatgt gaatttggac aacgaaatag acaatggact     180
ccatcccact gaggaccccg cgccgtgcga ctgcggtcag gagcactcgg aatgggacaa     240
gctcttcatc atgctggaga actcgcagat gagagagcgc atgctgctgc aagccacgga     300
cgacgtcctg cggggcgagc tgcagaggct gcgggaggag ctgggccggc tcgcggaaag     360
cctggcgagg ccgtgcgcgc cggggctcc cgcagaggcc aggctgacca gtgctctgga     420
cgagctgctg caggcgaccc gcgacgcggg ccgcaggctg gcgcgtatgg agggcgcgga     480
ggcgcagcgc ccagaggagg cggggcgcgc cctggccgcg gtgctagagg agctgcggca     540
gacgcgagcc gacctgcacg cggtgcaggg ctgggctgcc cggagctggc tgccggcagg     600
ttgtgaaaca gctatttat tcccaatgcg ttccaagaag attttgaa gcgtgcatcc      660 agtgagacca atgaggcttg agtctttttag tgcctgcatt tgggtcaaag ccacagatgt     720
attaaacaaa accatcctgt tttcctatgg cacaagagg aatccatatg aaatccagct      780
gtatctcagc taccaatcca tagtgtttgt ggtgggtgga gaggagaaca aactggttgc     840
tgaagccatg gtttccctgg aaggtggac ccacctgtgc ggcacctgga attcagagga     900
agggctcaca tccttgtggg taaatggtga actggcggct accactgttg agatggccac     960
aggtcacatt gttcctgagg gaggaatcct gcagattggc caagaaaaga atggctgctg    1020
tgtgggtggt ggctttgatg aaacattagc cttctctggg agactcacag gcttcaatat    1080
ctgggatagt gttcttagca atgaagagat aagagagacc ggaggagcag agtcttgtca    1140
catccggggg aatattgttg ggtggggagt cacagagatc cagccacatg gaggagctca    1200
gtatgtttca taaatgttgt gaaactccac ttgaagccaa agaaagaaac tcacacttaa    1260
aacacatgcc agttgggaag gtctgaaaac tcagtgcata ataggaacac ttgagactaa    1320
tgaaagagag agttgagacc aatctttatt tgtactggcc aaatactgaa taaacagttg    1380
aaggaaagac attggaaaaa gctt                                            1404
```